United States Patent [19]

Esmond

[11] 4,140,635
[45] Feb. 20, 1979

[54] PURIFICATION DEVICE

[76] Inventor: William G. Esmond, 800 Country Club Rd., Havre de Grace, Md. 21078

[21] Appl. No.: 787,300

[22] Filed: Apr. 13, 1977

[51] Int. Cl.² .......................... A61M 1/03; B01D 19/00
[52] U.S. Cl. .......................................... 210/177; 55/169; 55/255; 128/DIG. 3; 261/DIG. 28; 210/186; 210/188; 210/295; 210/420; 422/46; 422/47
[58] Field of Search .................... 23/258.5 R, 258.5 A, 23/258.5 B, 258.5 BH; 128/DIG. 3; 55/169, 255; 261/DIG. 28; 210/177, 186, 188, 295, 420

[56] References Cited

U.S. PATENT DOCUMENTS

| | | | |
|---|---|---|---|
| 2,705,493 | 4/1955 | Malmros et al. | 23/258.5 A |
| 2,927,582 | 3/1960 | Berkman et al. | 23/258.5 A |
| 3,204,631 | 9/1965 | Fields | 23/258.5 BH UX |
| 3,437,450 | 4/1969 | Greenwood | 23/258.5 A |
| 3,615,238 | 10/1971 | Bentley et al. | 23/258.5 BH |
| 3,717,174 | 2/1973 | DeWall | 23/258.5 A X |
| 3,769,162 | 10/1973 | Brumfield | 23/258.5 BH X |
| 3,898,045 | 8/1975 | Bowley | 23/258.5 BH |
| 3,907,504 | 9/1975 | Hammond et al. | 23/258.5 A |
| 3,946,731 | 3/1976 | Lichtenstein | 23/258.5 R X |
| 4,033,724 | 7/1977 | Tamiya | 23/258.5 BH |
| 4,073,622 | 2/1978 | Luppi | 23/258.5 BH |

FOREIGN PATENT DOCUMENTS 1146619  4/1963  Fed. Rep. of Germany ..... 23/258.5 A

OTHER PUBLICATIONS

Esmond et al., "Profound Hypothermia . . . of High Efficiency"; J. Thoracic & Cardiovascular S.; vol. 42, No. 5, 11/61, pp. 563-574.
Lewis et al., "Semiautomatic Control . . . Blood Pump"; J. Thoracic and Cardiovascular S.; vol. 43, No. 3, 3/62, pp. 392-396.
Lopez Belio et al.; "High Output Bubble . . . Bypass", Surgery; vol. 47, No. 5, 5/60, pp. 772-783.

Primary Examiner—Barry S. Richman
Attorney, Agent, or Firm—Charles E. Brown

[57] ABSTRACT

A purification device for utilizing a gas to purify a liquid, principally useable as an artificial lung, and employs a simple mixing tube so as to assure the mixing of a purification gas with the liquid, with the liquid and gas mixture exiting from the mixing tube into a housing carrying gas separation means in the form of a filter with the purified liquid flowing through the housing in reverse direction to liquid flow in the mixing tube and being collected at one end of the housing while the separated gas is vented from the opposite end of the housing. The housing carries a heat exchange device for maintaining the purified liquid at a predetermined temperature as it exits from the purification device. A pump is provided for pumping the purified liquid from the housing. In order that the housing will not be pumped dry, there is provided a float valve arrangement for controlling flow of the purified liquid out of the housing.

10 Claims, 14 Drawing Figures

U.S. Patent Feb. 20, 1979 4,140,635
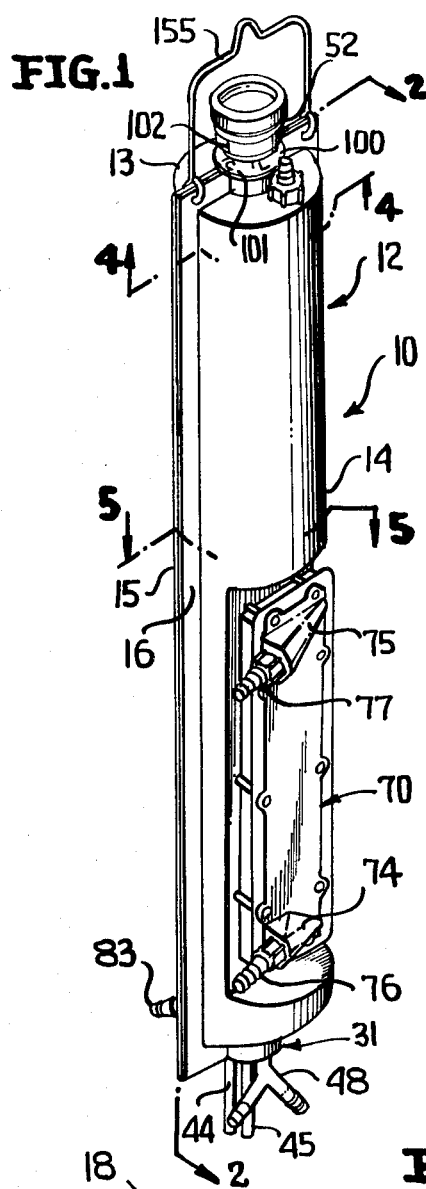
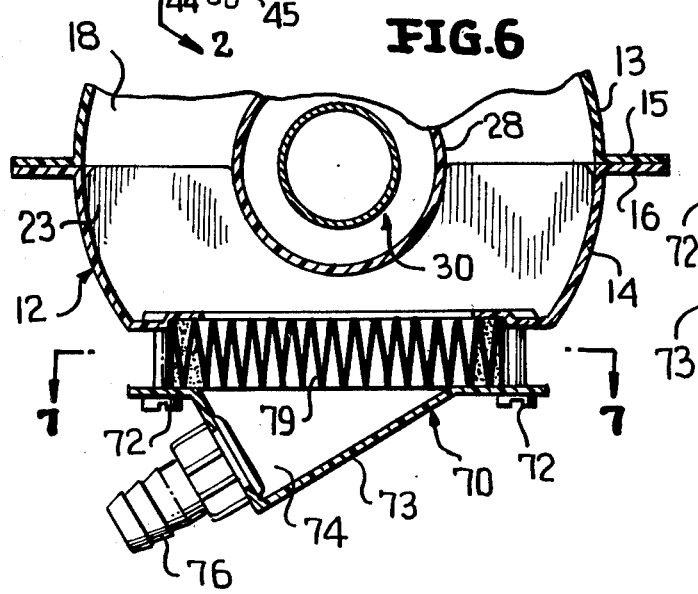
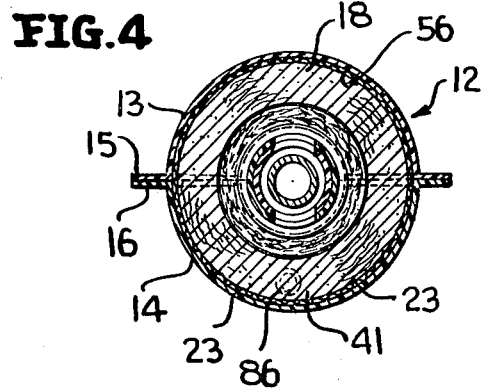
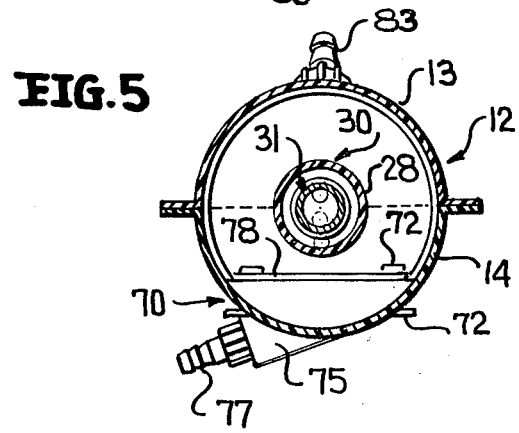
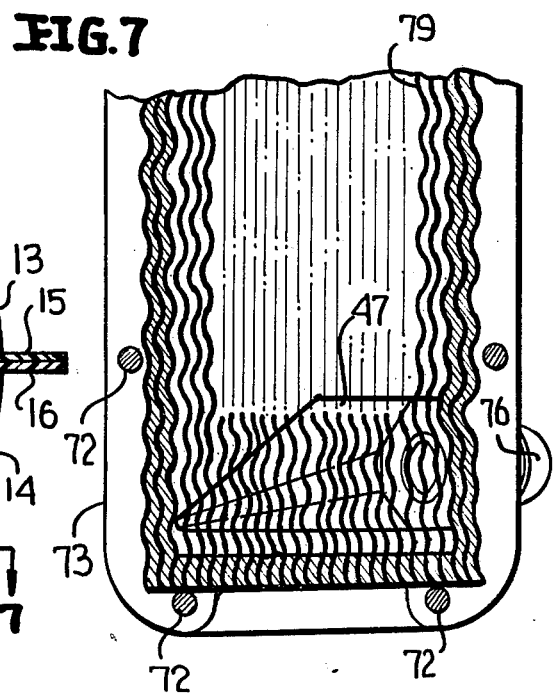

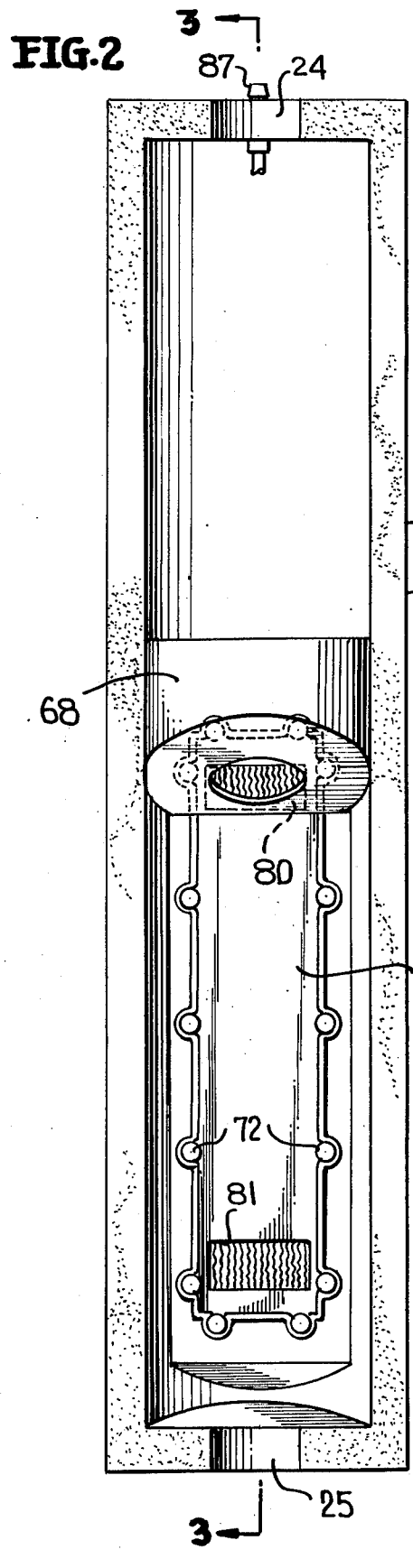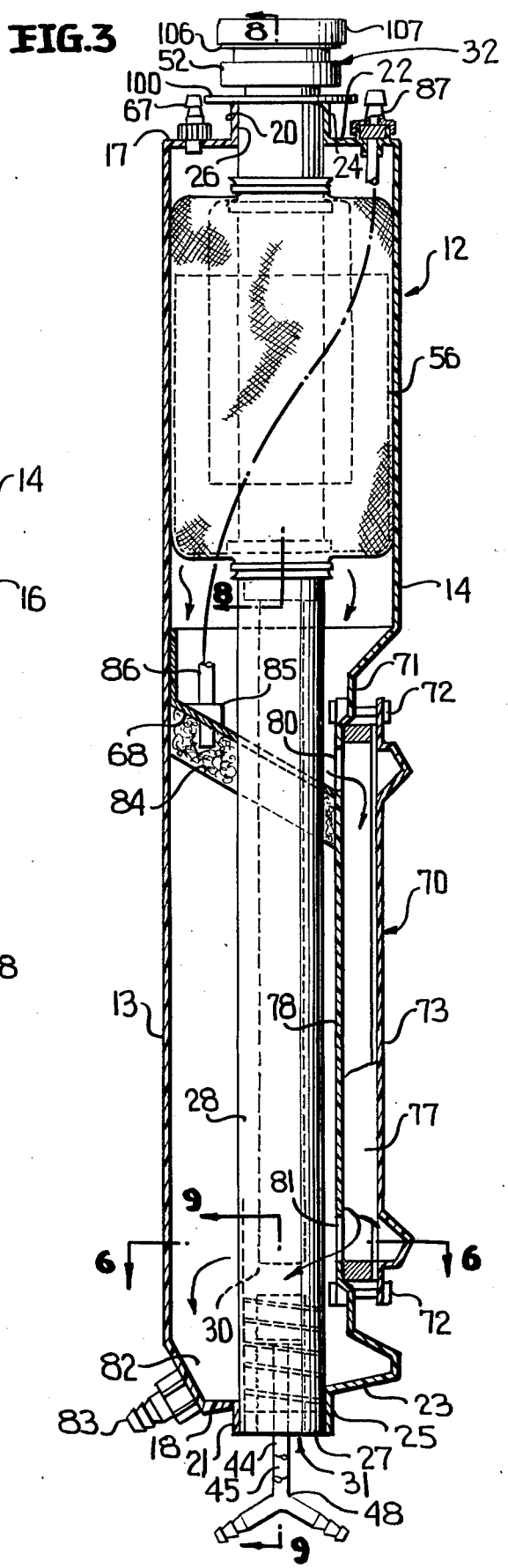

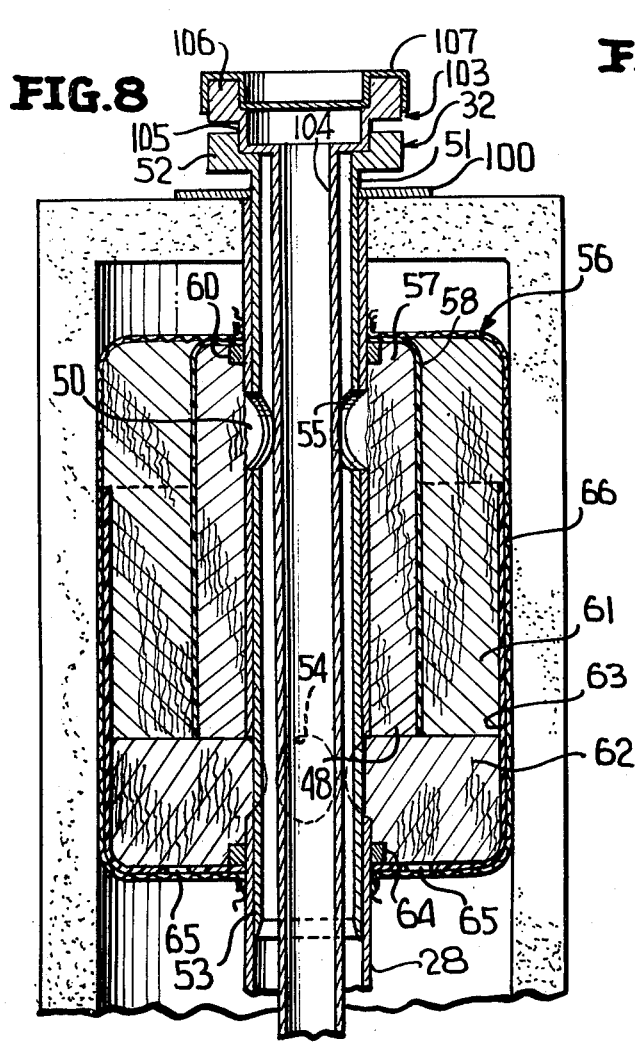
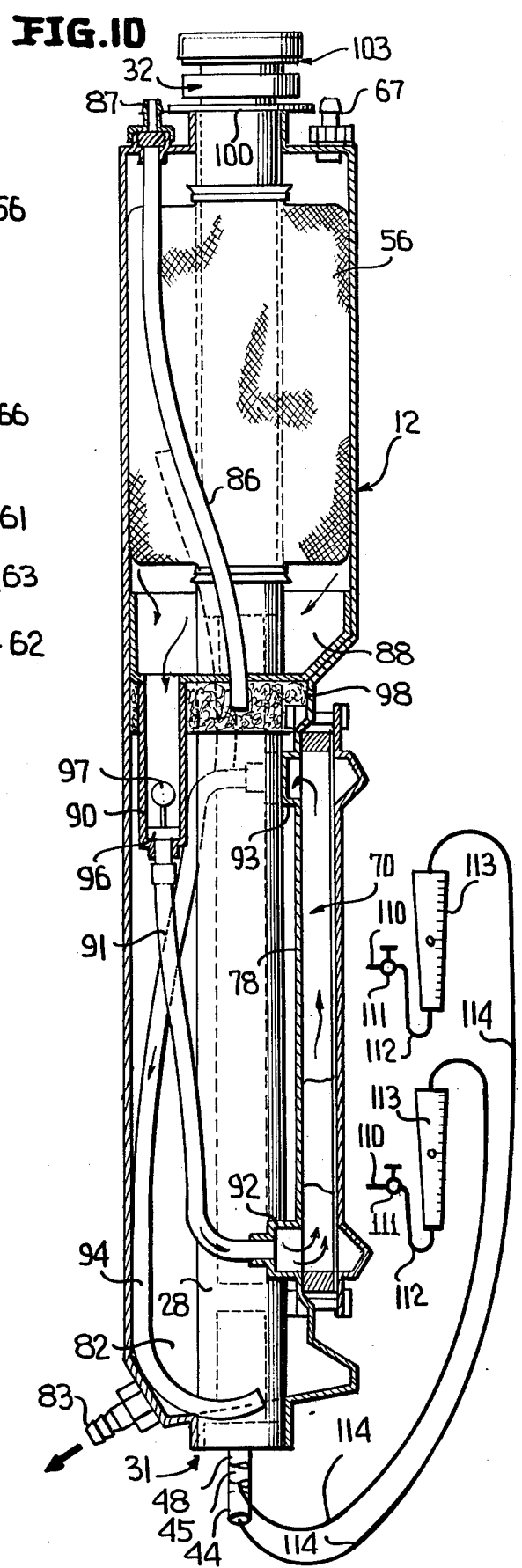
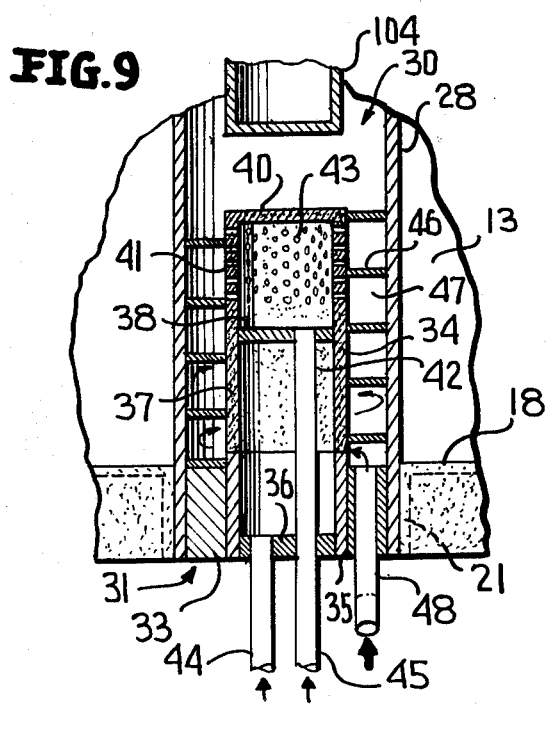

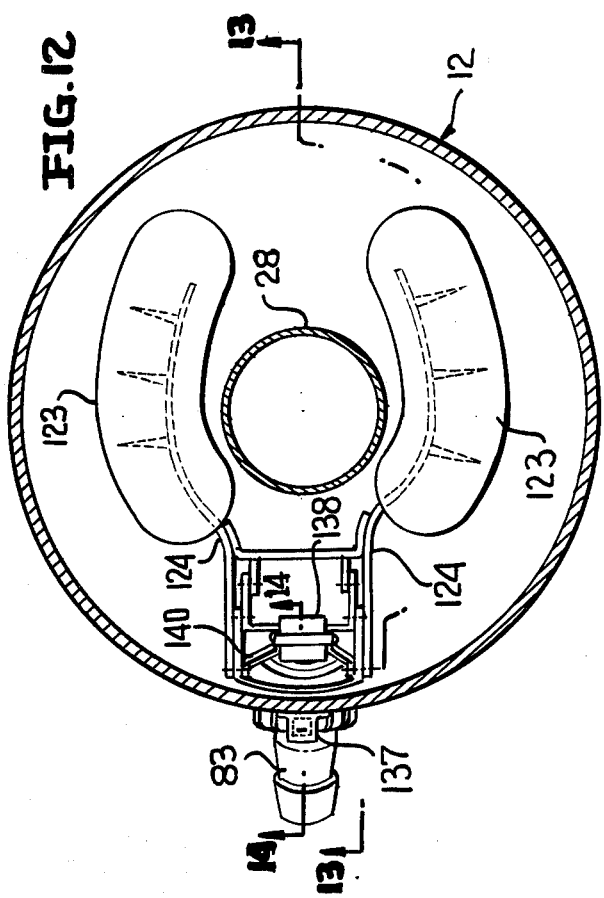
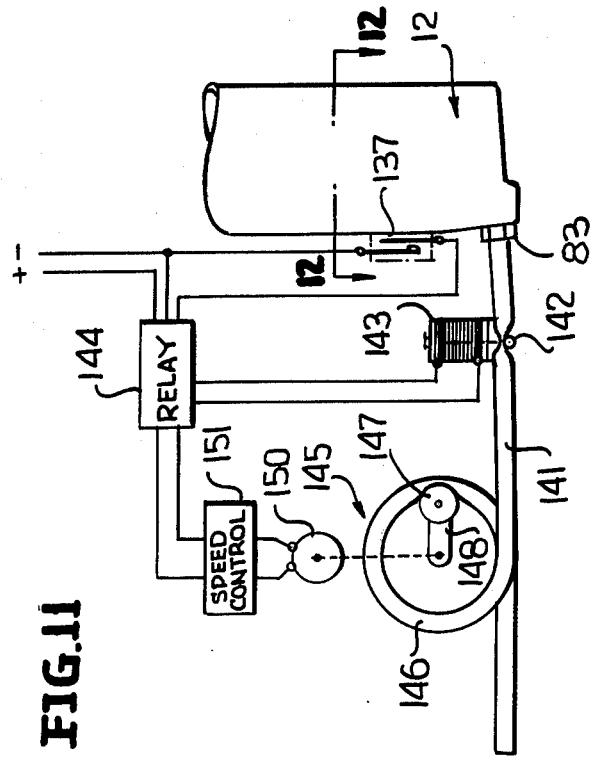
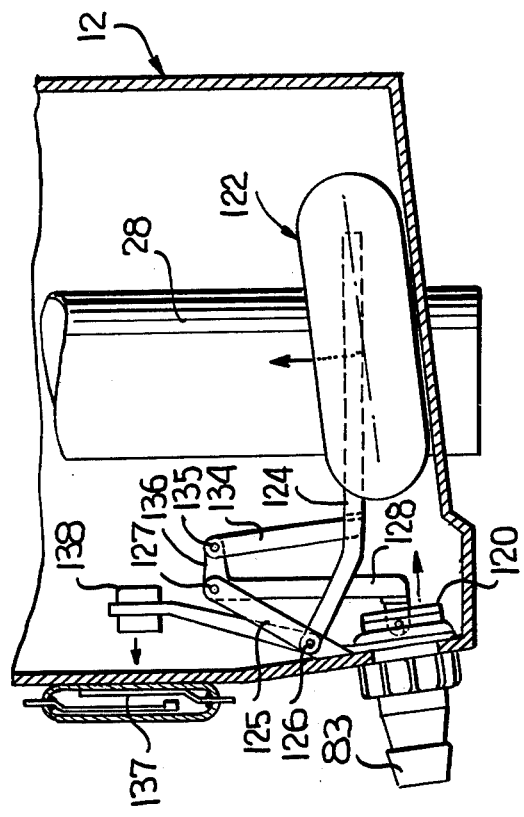
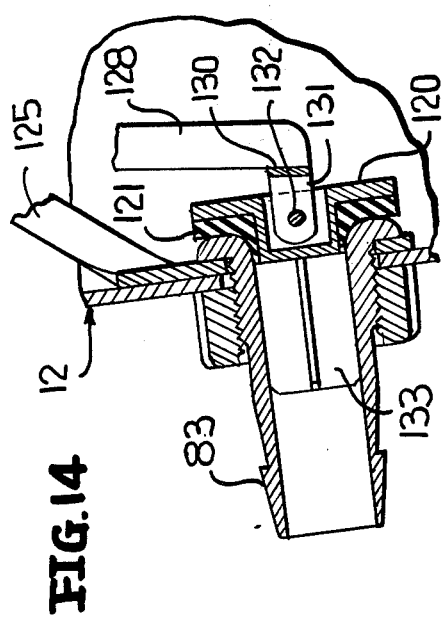

4,140,635

PURIFICATION DEVICE

This invention relates to new and useful improvements in purification devices, and more particularly to a purification device of the artificial lung type.

BACKGROUND OF THE INVENTION

It is well known to provide purification devices which utilize a gas to purify a liquid, such devices being frequently utilized in the purification of blood by flowing oxygen through the blood with the oxygen regenerating the blood and driving off carbon dioxide and other contaminants carried by the blood. In the past, such purification devices have been partly of inappropriate construction and have failed to meet many of the desired qualifications of a proper artificial lung.

SUMMARY OF THE INVENTION

In accordance with this invention, there is provided a potentially disposable, single use, purification device which is readily suitable for use as an artificial lung with the device being formed of two simple molded housing halves formed of a suitable plastic material, the housing halves defining at opposite ends of the housing aligned centrally located sockets. An elongated tube extends between the housing halves with the ends thereof seated in the sockets. The opposite ends of the tube are plugged with the plug at the one end of the tube carrying supply lines for a liquid and a gas and the tube being provided adjacent the opposite end thereof with a suitable outlet opening into the housing.

The simple tube, while being of a simple and inexpensive construction, provides an excellent mixing chamber. The tube must be filled with the liquid before the liquid flows through the outlet of the tube and the purification gas is diffused as it enters into the liquid so as to provide for a maximum mixing of the purification gas with the liquid.

When the liquid-gas mixture exits from the mixing tube, it flows into the relatively large volume of the housing under practically no pressure with the result that the gas entrained therein is free to escape. Further, as the liquid-gas mixture flows towards a collection point in the housing, it passes through suitable gas separating means in the form of filter material which provides for an effective scrubbing of the liquid and the removal of gas therefrom and a second filter to remove silicon anti-foam oil from the blood. Thus an effective purification of the blood is obtained.

A further feature of the invention is the provision of a maximum efficiency Esmond MAXICAL (TM) heat exchanger in the housing adjacent the collection point for the liquid to permit safe induction and recovery from hypothermia. The housing and heat exchanger are so related wherein substantially all of the liquid must pass through the heat exchanger and thus the collected liquid may be maintained at or adjusted to a precisely predetermined temperature. In the case of blood, this is critical so as to avoid patient hypothermia. The design provides a flow pattern that assures the device will operate with the least prime possible while at the same time incorporating safety features to prevent the unit from being pumped dry.

With the above and other objects in view that will hereinafter appear, the nature of the invention will be more clearly understood by reference to the following detailed description, the appended claims and the several views illustrated in the accompanying drawings:

IN THE DRAWINGS

FIG. 1 is a perspective view of the purification device and illustrates the general details thereof.

FIG. 2 is a longitudinal sectional view taken between the split halves of the housing and shows generally the details of the internal construction of the purification device.

FIG. 3 is a longitudinal sectional view taken along the line 3—3 of FIG. 2 and shows further the details of the purification device.

FIG. 4 is a transverse sectional view taken along the line 4—4 of FIG. 1,

FIG. 5 is a transverse sectional view taken along the line 5—5 of FIG. 1 and

FIG. 6 is an enlarged fragmentary transverse sectional view taken along the line 6—6 of FIG. 3, all showing further constructional details of the purification device.

FIG. 7 is an enlarged fragmentary longitudinal sectional view taken along the line 7—7 of FIG. 6 and shows further the details of the heat exchanger.

FIG. 8 is an enlarged fragmentary longitudinal sectional view taken along the line 8—8 of FIG. 3 and shows specifically the details of the gas separating means.

FIG. 9 is an enlarged fragmentary longitudinal sectional view taken along the line 9—9 of FIG. 3 and shows most specifically the details of the supply means for the liquid and gas.

FIG. 10 is a longitudinal sectional view similar to FIG. 3 showing a slightly modified form of the invention.

FIG. 11 is a fragmentary schematic elevational view showing pump means for removing purified liquid from the device.

FIG. 12 is a transverse horizontal sectional view taken through the lower portion of the housing generally along the line 12—12 of FIG. 11 and shows more specifically the details of a float valve assembly in the interior of the housing.

FIG. 13 is an enlarged fragmentary vertical sectional view taken along the line 13—13 of FIG. 12 and shows further the details of the float control assembly.

FIG. 14 is an enlarged fragmentary vertical sectional view taken along the line 14—14 of FIG. 12 and shows specifically the details of the valve part of the float control assembly.

Referring now to the drawings in detail, it will be seen that there is shown the purification device which is the subject of this invention, the purification device being generally identified by the numeral 10. The purification device 10 includes an upright housing, which is generally identified by the numeral 12 and which includes housing halves 13 and 14. The housing halves 13 and 14 are each generally of a semi-cylindrical configuration and each is provided with a peripheral flange 15, 16, respectively, which may be secured together by means of a suitable adhesive or other securing means.

Referring now to FIG. 3, it will be seen that the housing half 13 is provided with upper and lower end walls 17, 18 which have half circular notches therein defined by part cylindrical portions 20, 21 of the flange 15. The housing half 14 is also provided with upper and lower ends 22, 23 which have part cylindrical notches formed therein with the notches being defined by part cylindrical portions 24, 25 of the flange 16. The flange portions 20 and 24 combine to define at the upper end of the housing 12 a socket 26 while the flange portions 21 and 25 combine to define a socket 27 at the lower end of the housing 12.

An elongated tube 28 extends through the center of the housing 12 and has end portions thereof projecting out through the housing 12 and seated in the sockets 26, 27. The tube 28 defines an elongated mixing chamber generally identified by the numeral 30.

It is to be understood that once the mixing chamber 30 has been positioned between the housing halves 13, 14 and the housing halves 13, 14 are sealed together, the mixing chamger 30 will be automatically positioned within the housing 12.

The tube 28, as viewed in FIG. 3, is closed at the lower end thereof by means of a plug or closure 31. A second closure 32 closes the upper end of the tube 28. Referring to FIG. 9, it will be seen that the closure 31 includes a plug 33 which carries centrally thereof a tube 34. The tube 34 has an imperforate lower portion 35 seated in the plug 33 and has the lower end thereof closed by means of a relatively thin plug 36. The tube lower portion 35 extends above the plug 33 and terminates in an intermediate portion 37 which is formed of sintered plastic material, such as sintered polypropylene so as to have very fine passages therethrough. The tube 34 is provided in the upper portion thereof with another thin plug 38 and the upper end of the tube 34 is closed by means of an end wall 40. Between the plug 38 and the end wall 40, there is a perforated tube portion 41 having larger passages therethrough.

At this time it is pointed out that the tube portion 37 and the plug 38 generally define a first chamber 42 while the plug 38, the end wall 40 and the tube portion 41 define a second chamber 43. A first gas line 44, which preferably has oxygen directed therethrough, is carried by the plug 36 and opens into the chamber 42. This gas passes out through the tube portion 37 in the form of very fine bubbles. A second tube 45, which preferably supplies oxygen also, extends through the plugs 36 and 38 and opens into the chamber 43. The gas within the chamber 43 passes thereout of through the tube portion 41 in the form of larger bubbles.

Disposed around the outside of the tube 34 and in sealed engagement with the inner surface of the tube 28 is a spiral baffle 46. The baffle 46 defines a spiral flow passage 47 for the liquid being treated, the liquid being preferably blood. A third tube 48 extends through the plug 33 outwardly of the tube 34 and opens into the spiral flow passage 47. The lower end of the tube 48 is bifurcated so that two liquid feed lines (not shown) may be simultaneously connected thereto. This is best shown in FIG. 3.

It will be understood that the liquid entering into the lower end of the mixing chamber 30 will have the oxygen or other gas bubbles difused therein. In the case of blood, oxygen will first of all cleanse the blood of excess $CO_2$ and then resupply the blood with the necessary oxygen.

The blood flows up within the tube 28 where the hemoglobin is fully oxygenated with oxygen.

At the upper end of the tube 28, there is provided a first set of diametrically opposed outlets 48 and an upper set of also diametrically opposed outlets 50. The closure 32 is in the form of a valve member and includes a shank 51 which is provided at the upper end thereof with a knob 52 to facilitate the turning thereof. The shank 51 has a sufficiently tight fit with the tube 28 so as to effectively seal the upper end of the tube 28. The shank 51 terminates in a tube portion 53 at its lower end and the tube portion 53 has a first set of diametrically opposed outlets 54 in the lower portion thereof and a second set of diametrically opposed outlets 55 in the upper protion thereof. The outlets 54 and 55 are rotated 90° with respect to each other so that when the outlets 55 are aligned with the outlets 50, the outlets 48 are closed by the tube 53, and vice versa. Thus by rotating the tube 53, flow out of the tube 28 can be selectively through the outlets 48 or the outlets 50.

In order to facilitate the rotational positioning of the tube 53, the upper portion of the housing 12 is provided with a collar 100 having suitable markings 101 thereon indicating as to whether the patient is a large patient or a small patient. Further, the knob 52 is provided with a marking 102 which is selectively alignable with the markings 101 to indicate the relative position of the tube portion 53 and the outlets 54 and 55 thereof.

Surrounding the upper part of the tube 28 are gas separating means, generally identified by the numeral 56. The gas separating means 56 includes a first cylinder 57 of uncoated filter material which extends about the tube 28 from above the outlets 50 down to just above the outlets 48. A polyethylene barrier sleeve 58 is telescoped over the cylinder 57 and has the upper portion thereof engaging the exterior of the tube 28. In order to position the sleeve 58, a collar 60 extends around the tube 28.

Telescoped over the sleeve 58 and the cylinder 57 is a second cylinder 61 of filter material. Below the cylinders 57 and 61 is a third cylinder 62 of filter material. The cylinder 62 is of an external diameter corresponding to the external diameter of the cylinder 61 and extends from the cylinders 57 and 61 down below the outlets 48. A second polyethylene barrier sleeve 63 extends from around the tube 28 up over the cylinder 62 and partially over the cylinder 61. A collar 64 is provided for the purpose of positioning the cylinder 62. The lower part of the sleeve 63 is provided with suitable openings 65 through which liquid may drain.

Encasing all of the cylinders and the sleeves is a dacron polyester knit sock 66 which is tied about the tube 28 above the collar 60 and below the collar 64. The sock 66 holds the various cylinders of filter material together and positions the same on the tube 28.

At this time it is to be understood that the filter material is to be compatible with the particular liquid being treated. Further, when the liquid being treated is blood, it is desirable that one of the cylinders, preferably the cylinder 61 have incorporated in the filter material thereof a silicon anti-foam. Also, the sock 66 should be treated with silicon anti-foam above the cylinder 62.

It is to be understood that when the outlets 50 are opened, the liquid being treated and gases must travel a long distance through the gas separating means 56 whereas when the outlets 48 are opened, the liquid and gases travel a much shorter distance. From a practical standpoint, the device is intended for the purpose of treating human blood and the long passage is utilized for large adults and the short passage for small adults.

It is to be understood that the same device may be utilized for babies and children. With reference to FIG. 8, it will be seen that inserted within the closure 52 is a volume reducing member 103. The volume reducing member 103 includes a tube portion 104 which is closed at its lower end and which extends down through the tube 28 to a point adjacent the lower end thereof, as is shown in FIG. 9. The volume reducing member 103 includes a shoulder portion 105 which is seated within the knob 52 and forms a seal therewith. Above the shoulder portion there is a knob 106 which corresponds to the knob 52. The knob 106 is utilized to position and withdraw the volume reducing member 103.

A removable closure member 107 is carried by the knob 106 and when the volume reducing member 103 is not utilized, the closure member 107 is fitted on the knob 52 in the same manner.

It is to be understood that when the volume reducing member 103 is utilized, the tube portion 53 is adjusted so as to control the length of the flow path in accordance with whether the patient is a baby or a child in the same manner described above in conjunction with small adults and large adults.

The upper end of the housing 12 is provided with a conventional vent 67 so that gases passing upwardly in the housing from the gas separating means 56 may be vented to the atmosphere. The vent 67 is preferably placed in the end wall of the housing half 13.

With reference to FIG. 3, it will be seen that at approximately mid-height, the housing 12 is provided with an internal baffle 68. The baffle 68 prevents the free flow of the treated liquid (blood) down into the lower part of the housing. The baffle 68 is positioned for directing the treated liquid into a heat exchanger, generally identified by the numeral 70, for the purpose of maintaining a constant temperature in the returning liquid. The heat exchanger 70 is a self-contained unit which is mounted exteriorily of the housing 12. The housing half 14 is provided with an outwardly opening recess 71 in which the heat exchanger 70 is mounted with the heat exchanger being secured to the exterior of the housing half 14 in sealed relation by means of suitable fasteners 72.

It is to be noted that the heat exchanger 70 includes an outer cover plate 73 which is configurated at the opposite ends thereof to define an inlet 74 and a discharge 75 to which an inlet fitting 76 and an outlet fitting 77, respectively, are connected, as is best shown in FIG. 1. The fittings 76 and 77 provide for the circulation of a suitable heat exchange liquid through the heat exchanger 70.

It is also to be noted that the heat exchanger 70 includes a heat exchange element 79 defined by a pleated sheet, preferably metal, the pleating being in transverse section, as is clearly shown in FIG. 6. The heat exchange element 79 defines flow passages on the opposite sides thereof, the outer flow passages receiving the heat exchange liquid and the inner flow passages receiving the liquid being treated. It is further to be noted that the pleating of the sheet to form the heat exchange element 79 results in the forming of oppositely facing ribs and these ribs are curved in a sinisoidal manner in plan, as shown in FIG. 7 so that the flow passages are of a reversing arcuate configuration. This prevents laminar flow of the liquids within the flow passages and causes a mixing of the liquid on each side of the exchange element 79 as it flows in its respective passages so as to provide for a maximum heat exchange through the heat exchange element 79.

It is to be understood that the recess 71 is in part formed by a generally planar wall 78 of the housing half 14. The wall 78 opposes the heat exchange element 79 and is provided adjacent the upper end thereof with an inlet opening 80. The inlet opening 80 is disposed above the lower end of the baffle 68 so that the treated liquid is directed into and through the heat exchange element by the baffle 68.

An outlet opening 81 is formed in the lower part of the wall 78 with a liquid flowing there out of being directed into a lower sump portion 82 of the housing 12 and out through a discharge fitting 83. It will be apparent that the treated liquid is collected as soon as it is discharged from the heat exchanger 70 so that it will have very little temperature loss between the heat exchanger 70 and the point of discharge thereof from the device 10.

It is to be understood that there may be some gases remaining in the treated liquid after it passes out of the heat exchanger 70. These gases will flow upwardly in the lower half of the housing 12 and must be vented. Accordingly, filter material 84 is disposed below the baffle 80 and a vent fitting 85 is provided through the baffle 68. A vent line 86 extends through the upper part of the housing 12 and is coupled to a vent fitting 87.

Reference is now made to FIG. 10 wherein a slightly modified form of housing construction is illustrated. It is to be noted that in lieu of the sloping baffle 68, the housing 12 is provided with a horizontal baffle 88 which is generally cup-shaped. The baffle 88 is provided with a sump 90 to which a tube 91 is connected. The tube 91 has the lower end thereof connected to an inlet fitting 92 into the heat exchanger 70. The flow of the treated liquid through the heat exchanger 70 is vertically upwardly as opposed to downwardly in the case of the first illustrated form of the invention. The wall 78 is provided with an upper outlet fitting 93 to which a discharge tube 94 is connected. The discharge tube 94 directs the treated liquid down into the sump 82 to the discharge fitting 83 to avoid splashing and refoaming.

Under the baffle 88 is a layer of filter material 95. The vent tube 86 extends down through the baffle 88 into the filter material 95.

Reference is now made to FIG. 10 wherein there are illustrated conventional means for controlling the flow of oxygen into the tubes 44, 45. Associated with each of the tubes 44, 45 is a main oxygen supply 110 which is provided with a shut off valve 111 controlling flow to a tube 112, which, in turn, is connected to a conventional flow control device 113 having a discharge into a tube 114 which is connected to a respective one of the tubes 44, 45.

It is to be understood that it is highly desirable that only liquid (blood) be pumped from the bottom of the housing 12. Accordingly, as is shown in FIGS. 11 through 14, suitable pump and control means are provided. First of all, with respect to the outlet fitting 83, as is shown in FIG. 14, there is associated with the inner end thereof a valve member 120 which is provided with a sealing ring 121. The valve member 120 is float actuated by means of a float 122 which includes two float sections 123 disposed on opposite sides of the tube 28 and interconnected by means of link elements 124. The link elements 124 are pivotally mounted on support arms 125 which extend upwardly from a wall of the housing 12 about pivots 126. The support arms 125 carry at their upper ends pivots 127 on which upper ends of crank arms 128 are pivotally mounted. The lower ends of the crank arms 128, as is best shown in FIG. 14, are interconnected by a cross bar 130 which, in turn, has an arm 131 extending therefrom into a recess in the valve member 120, the arm 131 being pivotally connected to the valve member 120 by a pivot 132. At this time it is pointed out that the valve member 120 is guided with respect to the fitting 83 by means of a spider 133.

Returning to FIG. 13, it will be seen that the link elements 124 carry levers 134 which are connected to pivots 135 carried by arms 136 forming upper portions of the crank arms 128. Thus when the float elements 123 raise due to the existence of a liquid in the bottom part of the housing 12, the valve element 120 is moved to the right and the fitting 83 is opened for the discharge of liquid from within the housing 12.

At this time it is also pointed out that mounted on the outside of the housing 12 is a conventional reed switch 137. The reed switch 137 is open when the float 122 is in its lower position, but is closed by a magnet 138 carried by arms 140 which, in turn, are fixably secured to the inner ends of the link elements 124. When the float 122 moves upwardly in response to the existence of liquid within the bottom of the housing 12, the magnet 138 moves against the housing wall and exerts a sufficient electromagnetic force through the housing wall to effect the closing of the contacts of the reed switch 137.

At this time it is pointed out that the float elements 123 are preferably formed of a closed cell foamed material. It is also to be noted that the magnet 138 is so positioned that when it engages the wall of the housing 12 it stops the upward movement of the float elements 123.

Referring now to FIG. 11 it will be seen that extending from the fitting 83 is a readily deformable discharge line 141 which is provided adjacent the fitting 83 with a clamp 142 for closing the same. The clamp 142 is actuated by an electromagnetic device 143 in a conventional manner. The reed switch 137 controls the closing of a relay 144 which, in turn, controls the energization of the electromagnetic device 143.

There is also associated with the discharge line 141 a pump mechanism generally identified by the numeral 145 and whose operation is controlled by the relay 144 through the switch 137. While any suitable type of pump may be utilized, it is preferred that the pump be formed by a loop 146 of the discharge tube 141 and that there be associated with the loop 146 a compressing roller 147 which serves to collapse the tube 141 and thus effect a continuous pumping of a liquid therethrough. The roller 147 is carried by a crank arm 148 of a motor device 150 which is preferably provided with a speed controller 151.

It will be readily apparent that the pump device 145 will provide for a continuous pumping action and therefore eliminate any voids in the liquid being pumped.

It is intended that the device be hung in a vertical position and, as is best shown in FIG. 1, the upper end of the housing 12 is provided with a suitable suspension device 155.

It is to be understood that the various components of the purification device are to be compatible with the liquid being purified. This is particularly true when the purification device is being utilized as an artificial lung. It is to be readily apparent that a reaction with the blood by the elements of the purification device must be avoided. Therefore, the various components of the purification device 10, when utilized as an artificial lung, must be made of suitable materials which are known to be compatible with blood (polyethylene, polypropylene, lexan polycarbonate, vinyl, styrene, etc.).

Although preferred embodiments of the purification device have been specifically illustrated and described herein, it is to be understood that minor modifications may be made therein without departing from the spirit and scope of the invention, as defined by the appended claims.

I claim:

1. A purification device comprising a hollow housing, a mixing chamber extending through said housing, supply means for delivering a liquid to be purified and a purification gas to said mixing chamber at one end thereof, outlet means at the other end of said mixing chamber opening into said housing, gas separating means within said housing for effecting removal of gas from said liquid, liquid collection means at an end of said housing remote from said outlet means, and a gas vent at the opposite end of said housing, said mixing chamber being in the form of an elongated tube having closure means at opposite ends thereof, said supply means being carried by one of said closure means, and said one closure means including a plug member having a central tube extending axially inwardly therefrom, a spiral baffle extending longitudinally around said central tube and in combination with said elongated tube defining a spiral flow passage for a liquid to be purified, a liquid supply fitting carried by said plug and opening into said spiral flow passage, and gas flow means carried by said central tube for directing a purification gas into said spiral flow passage.

2. The device of claim 1 wherein said gas flow means includes means for directing fine gas bubbles and larger gas bubbles into said spiral flow passage.

3. The device of claim 1 wherein said gas flow means includes means for directing fine gas bubbles and larger gas bubbles into said spiral flow passage in sequence.

4. The device of claim 1 wherein said gas flow means includes a transverse baffle dividing said central tube into two separate chambers, a separate gas supply line opening into each of said chambers, said central tube having a first portion defining a wall of one of said chambers with said first portion having fine passage therethrough for directing fine gas bubbles from said one chamber into said spiral flow passage, and said central tube having a second portion defining a wall of the other of said chambers with said second portion having larger passages therethrough for directing larger gas bubbles from said other chamber into said spiral flow passage.

5. A purification device comprising a hollow housing, a mixing chamber extending through said housing, supply means for delivering a liquid to be purified and a purification gas to said mixing chamber at one end thereof, outlet means at the other end of said mixing chamber opening into said housing, gas separating means within said housing for effecting removal of gas from said liquid, liquid collection means at an end of said housing remote from said outlet means, and a gas vent at the opposite end of said housing, said mixing chamber being in the form of an elongated tube having closure means at opposite ends thereof, said outlet means including first and second longitudinally spaced outlets in said elongated tube, said closure means including a tubular control valve telescoped within said elongated tube and movable relative to said elongated tube to selectively open one of said spaced outlets while simultaneously closing the other, and said gas separating means defining an elongated passage surrounding said elongated tube and extending longitudinally beyond said spaced outlets in both directions, said elongated passage having an inner portion adjacent said elongated tube and a reverse direction outer portion surrounding said inner portion whereby the effective length of said elongated passage may be varied in accordance with the outlet selected, said gas separating means including a first cylinder of filter material directly surrounding said elongated tube, a first barrier sleeve extending from an upper portion of said elongated tube down over said first cylinder but terminating short of a lower one of said outlets, a second cylinder of filter material telescoped over said first barrier sleeve and a second barrier sleeve extending from said elongated tube below said lower outlet up and around said second cylinder, said barrier sleeves defining said elongated passage.

6. The device of claim 5 wherein a knitted sock encloses said cylinders and sleeves.

7. The device of claim 5 wherein a third cylinder of filter material surrounds said elongated tube below said first and second cylinders and said first barrier sleeve, and said second barrier sleeve extends below said third cylinder.

8. A purification device comprising a hollow housing, a mixing chamber extending through said housing, supply means for delivering a liquid to be purified and a purification gas to said mixing chamber at one end thereof, outlet means at the other end of said mixing chamber opening into said housing, gas separating means within said housing for effecting removal of gas from said liquid, liquid collection means at an end of said housing remote from said outlet means, and a gas vent at the opposite end of said housing, said mixing chamber being in the form of an elongated tube having closure means at opposite ends thereof, said outlet means including first and second longitudinally spaced outlets in said elongated tube, said closure means including a tubular control valve telescoped within said elongated tube and movable relative to said elongated tube to selectively open one of said spaced outlets while simultaneously closing the other, and said gas separating means defining an elongated passage surrounding said elongated tube and extending longitudinally beyond said spaced outlets in both directions, said elongated passage having an inner portion adjacent said elongated tube and a reverse direction outer portion surrounding said inner portion whereby the effective length of said elongated passage may be varied in accordance with the outlet selected, a space reducing member removably telescoped through said tubular control valve and down into said elongated tube; said space reducing member adapting said device for use with babies and children.

9. The device of claim 8 wherein said control valve and said space reducing member have identical free end portions, and including a closure cap interchangeably mountable on said free end portions removably carried by said end portion of said space reducing member.

10. A purification device comprising a hollow housing, a mixing chamber extending through said housing, supply means for delivering a liquid to be purified and a purification gas to said mixing chamber at one end thereof, outlet means at the other end of said mixing chamber opening into said housing, gas separating means within said housing for effecting removal of gas from said liquid, liquid collection means at an end of said housing remote from said outlet means, and a gas vent at the opposite end of said housing, wherein a highest efficiency heat exchanger is provided in the general path of collected liquid adjacent said liquid collection means, said heat exchanger being mounted exteriorly of said housing in sealed relation thereto, and said housing having liquid outlet and inlet passages in communication with said heat exchanger, said housing having a baffle member therein adjacent and heat exchanger for assuring liquid flow through said housing liquid outlet into said heat exchanger, filter material positioned on the underside of said baffle member for preserving sterility and for preventing liquid loss, and a vent line extending from within said filter material through said baffle member and out through an upper end of said housing.

* * * * *